United States Patent
Shechter Ushpizin et al.

(10) Patent No.: US 12,150,772 B2
(45) Date of Patent: Nov. 26, 2024

(54) METHODS AND DEVICE FOR DETERMINING EFFICIENCY OF LACTATION

(71) Applicant: MYMILK LABORATORIES LTD., Herzliya (IL)

(72) Inventors: Ravid Shechter Ushpizin, Glil Yam (IL); Sharon Haramati, Herzliya (IL)

(73) Assignee: MYMILK LABORATORIES LTD., Herzliya (IL)

( * ) Notice: Subject to any disclaimer, the term of this patent is extended or adjusted under 35 U.S.C. 154(b) by 700 days.

(21) Appl. No.: 17/426,523

(22) PCT Filed: Jan. 28, 2020

(86) PCT No.: PCT/IL2020/050106
§ 371 (c)(1),
(2) Date: Jul. 28, 2021

(87) PCT Pub. No.: WO2020/157751
PCT Pub. Date: Aug. 6, 2020

(65) Prior Publication Data
US 2022/0087594 A1   Mar. 24, 2022

Related U.S. Application Data

(60) Provisional application No. 62/953,220, filed on Dec. 24, 2019, provisional application No. 62/797,385, filed on Jan. 28, 2019.

(51) Int. Cl.
A61B 5/00 (2006.01)
A23L 33/00 (2016.01)

(52) U.S. Cl.
CPC .......... *A61B 5/4288* (2013.01); *A61B 5/4312* (2013.01); *A23L 33/40* (2016.08)

(58) Field of Classification Search
None
See application file for complete search history.

(56) References Cited

U.S. PATENT DOCUMENTS

2010/0292604 A1* 11/2010 Kapon ................ A61B 5/4312
                                                                600/547
2018/0160952 A1*  6/2018 Hsieh .................. A61B 5/6823

OTHER PUBLICATIONS

Miller, "Part 3 Relationship to Adequacy of Lactation", published Aug. 26, 1951, Retrieved from NIH, pp. 1-5 (Year: 1951).*
Cregan M. D. Initiation of lactation in women after preterm delivery Acta Obstet Gynecol Scand. Sep. 2002;81(9):870-7.
Galipeau et al. Infant and Maternal Factors Influencing Breastmilk Sodium Among Primiparous Mothers. Breastfeed Med. 2012.
Kermack W. O and Miller, R.A, the electrical conductivity and chloride content of women's milk, Arch. Disease, Childhood 1950.
Mashahiko M, The relation between breast milk sodium to potassium ratio and maternal report of a milk supply concern. The Journal of Pediatrics, 2016.

(Continued)

*Primary Examiner* — Devin B Henson
*Assistant Examiner* — Matthew Eric Ogles
(74) *Attorney, Agent, or Firm* — The Roy Gross Law Firm, LLC; Roy Gross

(57) ABSTRACT

The invention generally concerns methods and devices for determining inadequate lactation in female subject.

19 Claims, 10 Drawing Sheets

(56) References Cited

OTHER PUBLICATIONS

Morton. The Clinical Usefulness of Breast Milk Sodium in the Assessment of Lactogenesis. Pediatrics 1994.
Neville & Morton; Physiology and Endocrine Changes Underlying Human Lactogenesis II J. Nutr. 131: 3005S-3008S, 2001.
W. O. Kermack and R. A. Miller, Arch Dis Child. Jun. 1951.; 26(127): 265-269. (pp. 267-268).
R. A. Miller, Arch Dis Child Actions, 1951, vol. 26(128):325-329 (pp. 325-328).
R. A. Miller, Edinb. Med. J. 1952, 59(5): 238-246 (pp. 244-245).
Lisa Gatti, of Nursing Scholarship, 2008 vol. 40; Iss. 4. , p. 361.
S S Humenick , P D Hill, J Thompson, A M Hart, Can J Nurs Res , 1998;30(3):67-81.
Kermack, W. O., Miller, R. A., Archives of Disease in Childhood. Aug. 1951.; vol. 26(128): 320-324. (p. 320).
Miller, R. A., Jackson, I. I. A. p. 329 Archives of Disease in Childhood. Aug. 1951.; vol. 26(128): 329-334.

\* cited by examiner

METHODS AND DEVICE FOR DETERMINING EFFICIENCY OF LACTATION

TECHNOLOGICAL FIELD

The present invention relates to methods and device for determining efficiency of lactation.

BACKGROUND

Human breast milk is considered as the gold standard in infant nutrition, promoting infant health and development and as such has been recommended by health authorities as the exclusive nutrition for the first 6 months of infant's life.

Proper lactation highly depends on the ability of the infant's mother to secrete milk. This process known as lactogenesis involves maturation of alveolar cells and takes place in two stages: an early secretory initiation stage during the second half of pregnancy and a later secretory activation stage II lactogenesis, that represent the onset of copious milk production after delivery.

Breastmilk production highly depends on stage II lactogenesis. During stage II lactogenesis milk secretion increase from less than 100 ml/day, at the first day postpartum to over 400-500 ml/day at day 3 after birth. This is accompanied by physiological changes in several breast epithelial processes, including changes in the permeability of the paracellular pathway between epithelial cells alongside changes in the secretion rate of milk components. Hence any delay in the initiation of stage II lactogenesis may have profound consequence of both short term lactation and long term lactation.

Lactogenesis III is generally considered as the transition from endocrine to autocrine control over milk production at the breast, at the following weeks of lactation.

Delay in the initiation of stage II, and inadequate lactogenesis III is not routinely diagnosed by healthcare professionals, but is rather diagnosed only in extremes. It is either identified by late clinical signs in the infant or by direct evaluation by a lactation consultant. It was previously suggested that the level of milk sodium may correlate with delayed lactogenesis or problems with milk-production (Morton 1994, Mashahiko, 2016, Galipeau, 2012; Neville & Morton 2001) as well as linked to insufficient milk production and delayed lactogenesis II (Galipeau, 2012, Cregan, 2002). Milk conductivity has been previously linked to successful breastfeeding at later stage after delivery. Previous studies have shown that the average conductivity in milk sample decreases with the breastfeeding stage (Kermack 1950).

Weaning process, is also reflected in milk composition, as a mirror process to lactogenesis.

BACKGROUND ART

Cregan M. D. Initiation of lactation in women after preterm delivery Acta Obstet Gynecol Scand. 2002 September; 81(9):870-7.

Galipeau et al. Infant and Maternal Factors Influencing Breastmilk Sodium Among Primiparous Mothers. Breastfeed Med. 2012.

Kermack W. O and Miller, R. A, the electrical conductivity and chloride content of women's milk, Arch. Disease, Childhood 1950 Mashahiko M, The relation between breast milk sodium to potassium ratio and maternal report of a milk supply concern. The Journal of Pediatrics, 2016.

Morton. The Clinical Usefulness of Breast Milk Sodium in the Assessment of Lactogenesis. Pediatrics 1994.

Neville & Morton; Physiology and Endocrine Changes Underlying Human Lactogenesis II J. Nutr. 131: 3005S-3008S, 2001.

GENERAL DESCRIPTION

Breast milk is a complex composition that comprises a large number of components, which changes dynamically between milk colostrum "the liquid gold" and mature milk, where different component dynamics act in opposing directions. The inventors have surprisingly found that despite the intrinsic complexity of human breast milk, the information from at least one physicochemical parameter as described herein provide an accurate prediction of an inadequate lactation. Specifically, the inventors of the technology disclosed herein have developed a computational model which can predict with a sensitivity of 73% (True positive identification) and a specificity of 80% (True negative), and with a Positive predictive value (PPV) of 92% lactation abnormalities at early stages after birth.

Breast milk feeding of infants has been recognized in recent years as an essential nutrition source for proper infant development. However, lactation is often negatively affected by various events that interrupt the normal development of the female breast or that interfere with the production of milk. For example, late onset of milk production, specifically copious milk production, has a negative effect on lactation ability and success. In the absence of appropriate tools that may assist mothers or care givers in identifying late or defected development of lactation, mothers as well as care givers are unable to predict and asses, and therefore prevent or lessen severity of difficulties which may develop.

The present invention is based on the finding that physicochemical parameters measured in breast milk, at various time points after delivery, can provide a powerful tool in determining lactation efficiency, specifically at an early stage after delivery. The findings at the basis of the invention subject of the present application are based on a large number of breast milk samples obtained from lactating women at different times after delivery. The data obtained included parameters relating to the milk samples as well as to the mothers from whom the samples were obtained. Such data included for example the degree of lactation (exclusive, partial or none), ease of lactation, type of delivery (natural or caesarean section), physiological condition of the mother at the time of sample collection, and others. The full set of information was combined to develop a high temporal resolution (hourly-based or day-based) computational model that provides information on the lactation efficiency, in real time, starting from the very early stages after delivery.

The computational model was able to accurately distinguish between adequate exclusive breastfeeding and a variety of conditions associated with inadequate lactation, for example, low milk production, delayed lactogenesis II (DLII) as well as physiological complications in the mother and in the infant. In addition, the computation model was used to estimate responsiveness to treatment.

The computation model utilizes at least the following two approaches:

In the first approach, the so-called "value approach", at least one physicochemical parameter is measured in a breast milk sample at a specific time after delivery (the first time point) and is compared to a predetermined value calculated by the computation model for the same time after delivery. In other words, according to this model—a physicochemical parameter (value) measured at a first time point in compared to a physicochemical value predetermined for the same time point. Where the measured and predetermined values are substantially the same, an adequate lactation is expected.

In the second approach, the so-called "time approach", the time point after delivery at which the physicochemical parameter is measured (the first time point) is compared to the time point after delivery calculated for the measured physicochemical parameter. In other words, in this model—the time points at which the physicochemical values are obtained are compared with the calculated time points. Where substantially identical time points associated with the physicochemical value are measured, an adequate lactation is expected.

Thus, a change in the measured value or time after delivery as compared with the model-based information is valuable in determining, for example, lactation efficiency, delayed lactogenesis II (DLII), inadequate lactogenesis III, milk production, or physiological complications in an exclusively breastfed infant and responsiveness to treatment.

Thus the invention provides a method for determining inadequate lactation in a female subject, the method comprising
  determining an expression of a physicochemical parameter of a breast milk sample obtained from the female subject at a time point after delivery, and
  determining whether the subject is inadequately lactating by comparing the expression of the physicochemical parameter of the breast milk sample with an expression of the physicochemical parameter of breast milk sample(s) obtained from adequately lactating female subjects at the time point after delivery, or by comparing a change in expression of a physicochemical parameter of two or more breast milk samples obtained at two or more time points, with a change of an expression of the physicochemical parameter of breast milk sample(s) obtained from adequately lactating subjects, at the two or more time points.

The invention further provides a method for determining inadequate lactation in a female subject, the method comprising
  determining an expression of a physicochemical parameter of a breast milk sample obtained from the female subject at a time point after delivery,
  determining an expression of the physicochemical parameter of breast milk sample(s) obtained from adequately lactating female subjects at the time point and
  determining whether the female subject is inadequately lactating.

In some embodiments, the step of determining whether the female is inadequately lactating is achieved by comparing the expression of a physicochemical parameter of a breast milk sample with an expression of the physicochemical parameter of breast milk sample(s) obtained from adequately lactating subjects at the time point.

In some embodiments, the step of determining whether the female is inadequately lactating is achieved by comparing a change in expression of a physicochemical parameter of two or more breast milk samples obtained at two or more time points, with a change of an expression of the physicochemical parameter of breast milk sample(s) obtained from adequately lactating subjects, at the two or more time points.

In some embodiments, the methods described herein comprise determining that the female subject is or is not adequately lactating at the time point after delivery based on the expression of the physicochemical parameter of breast milk sample(s) obtained from adequately lactating female subjects at the time point. In some further embodiments, the methods described herein comprise correlating a difference in the expression of the physicochemical parameter of a breast milk sample obtained from the female subject at a time point after delivery relative to the expression of the physicochemical parameter of breast milk sample(s) obtained from adequately lactating female subjects at the time point with inadequate lactation in the female subject.

The invention further provides a method for determining inadequate lactation in a female subject, the method comprising
  determining an expression of a physicochemical parameter of a breast milk sample obtained from the subject at a time point after delivery, and
  determining whether the subject is inadequately lactating by comparing the expression of a physicochemical parameter of a breast milk sample with an expression of the physicochemical parameter of breast milk sample(s) obtained from adequately lactating subjects at the time point, or by comparing a change in expression of a physicochemical parameter of two or more breast milk samples obtained at two or more time points, with a change of an expression of the physicochemical parameter of breast milk sample(s) obtained from adequately lactating subjects, at the two or more time points; wherein when the expression of the physicochemical parameter measured for the breast milk sample and the expression of the physicochemical parameter predetermined for the control population are not the same, the female subject has inadequate lactation.

The invention further provides a method for determining inadequate lactation in a female subject, the method comprising
  determining an expression of a physicochemical parameter of a breast milk sample obtained from the subject at a time point after delivery, and
  determining whether the subject is inadequately lactating by comparing the expression of the physicochemical parameter of the breast milk sample with an expression of the physicochemical parameter of breast milk sample(s) obtained from adequately lactating subjects at the time point, or by comparing a change in expression of a physicochemical parameter of two or more breast milk samples obtained at two or more time points, with a change of an expression of the physicochemical parameter of breast milk sample(s) obtained from adequately lactating subjects, at the two or more time points;
  wherein when the expression of the physicochemical parameter measured for the breast milk sample and the expression of the physicochemical parameter predetermined for the control population are same, or the physicochemical parameter for the breast milk sample is within 1.285SD of the expression of the same physicochemical parameter predetermined for the control population for the certain (same) time point, the female subject has adequate lactation.

In some embodiments, inadequate lactation in a female subject comprises or is associated with at least one of reduced lactation efficiency, delayed lactogenesis II (DLII), inadequate lactogenesis III or reduced milk production.

Further provided is a method for determining status of lactation in a female subject at a time point after delivery, the method comprising determining whether an expression of a physicochemical parameter of a breast milk sample obtained from the subject at a time point after delivery is different from an expression of the physicochemical parameter of breast milk sample(s) obtained from a control (retroactive) dataset from population of lactating subjects at the time point, wherein if the expression of the physicochemical parameter of the breast milk sample obtained from the subject is different from the expression of the same physicochemical parameter of breast milk sample(s) obtained from the control population, the female subject is regarded as having reduced lactation efficiency, delayed lactogenesis II (DLII), inadequate lactogenesis III or milk production.

In methods of the invention a differentiation may be made between adequately and inadequately lactating woman by determining whether the expression of the physicochemical parameter is different from that measured and thus predetermined for the time after delivery. Methods of the invention further provide the ability to measure a change in lactation over time, even where the initial indication or initial determination was of adequate lactation or inadequate lactation. A change over time may be detected based on early measurements and relative changes over time may be indicative of appearance or re-appearance of a medical condition, an improvement or worsening of a condition and other changes.

In some embodiments, methods of the invention comprise correlating a difference in the expression of the physicochemical parameter of a breast milk sample obtained from the female subject at a time point after delivery relative to the expression of the physicochemical parameter of breast milk sample(s) obtained from adequately lactating female subjects at the time point with inadequate lactation in the female subject.

As measurements may vary between a female's breasts, namely from one breast to another, such a difference may provide a indication of inadequate lactation in one of the female's breast and not in both. A female's breast adequate lactation may also be used as a control for determining inadequate lactation in the other breast or an indication to the appearance or re-appearance of a medical condition, an improvement or worsening of a condition and other changes in one or both of the female's breasts.

Where the expression of the physicochemical parameter of a breast milk sample obtained from the woman at a time point after delivery is different from an expression of the same physicochemical parameter of breast milk sample(s) obtained from a control population of lactating women at the same time point, the woman may be regarded as suffering from any of the conditions disclosed herein. The term "different" when used in connection with a measurable difference between the expressions determined for the breast milk sample and predetermined from the control population means a deviation from identity in expression. The deviation may be in the fact that the physicochemical parameter exists or does not exists, in the measurable size of the parameter and/or in the measurable value defining to the parameter. For example, where the physicochemical parameter is resistivity or conductivity, a different expression may be difference in the degree of conductivity or in the value measured for the sample as compared to the control population.

Within the context of the present application, the expression of the physicochemical parameter measured for the breast milk sample and the expression of the physicochemical parameter predetermined for the control population may be regarded same (not different) if the expression (e.g., value) of the physicochemical parameter for the breast milk sample is the same as the expression of the same physicochemical parameter or a range statistically predetermined based on the control population, or is within 1.285SD (standard deviation) of the average expression of the same physicochemical parameter predetermined for the control population.

In some embodiments, the expression of the physicochemical parameter measured for the breast milk sample and the expression of the physicochemical parameter predetermined for the control population may be regarded same (not different) if the expression (e.g., value) of the physicochemical parameter for the breast milk sample is within a range defined by a deviation of between 20% to 70% (or 20 to 30%, or 20 to 40%, or 20 to 50%, or 20 to 60%, or 30 to 40%, or 30 to 50%, or 30 to 70%, or 40 to 50%, or 40 to 60%, or 40 to 70%, or 50 to 60%, or 50 to 70%, or 60 to 70%) of the average expression of the same physicochemical parameter predetermined for the control population.

For example, the following steps were used to determine a physicochemical parameter, for e.g., electrical conductivity or electrical resistivity, predetermined for the control population:

milk samples from successful exclusively breastfeeding mothers were taken in various time points after birth (at least 6 mothers for each time frame), the women were with no apparent or reported problems (no report or diagnosis of excessive pain, breast inflammation, suspected low milk supply, inadequate baby weight gain) and have sustained successful breastfeeding in a follow-up period. For each of the samples, the electrical conductivity was measured.

for each time frame (each day separately for the first 2 weeks postpartum, three to seven days in the sequential weeks), the average value and standard deviation were calculated. The maximal normal value of conductivity for the specific time frame is average plus 1.28SD [80% of the full variation at each time point].

for each further tested female, milk was obtained from each breast separately and the measured value was compared to the value at the same time frame in the control group. Any increase from the maximal value at the control group was considered indicative of inadequate lactation, the extreme the deviation, the higher predictive alert for inadequate lactation. Thus, depending on the particular physicochemical parameter, the expression, e.g., value of the measured parameter, may be higher or lower, and thus different, from the expression of the same physicochemical parameter predetermined for the control population. In some cases, a higher expression of a particular physicochemical parameter may be indicative of inadequate lactation, while a lower expression of a different physicochemical parameter may be indicative of inadequate lactation. For example, wherein the physicochemical parameter is sodium concentration or sample conductivity, higher expressions relative to the control population are indicative of inadequate lactation. It should be noted that the greater the value, the higher is the risk for inadequate lactation. Alternatively, if the physicochemical parameter is electrical resistivity, lower expressions relative to the control population are indicative of inadequate lactation. It should be noted that the lower the value, the higher is the risk for inadequate lactation.

An expression of the predetermined physicochemical parameter may be expressed in the form of a graph, as shown for example in FIG. 4.

In some embodiments, methods of the invention comprise obtaining a milk sample from a female subject. In some embodiments, multiple milk samples are obtained from the subject at different time points. In some embodiments, the time point is the first time point, namely the earliest time at which a milk sample was obtained.

In some embodiments, methods of the invention comprise obtaining at least one breast milk sample from a female subject or obtaining at least one breast milk sample from one or both breasts of the female subject.

In some embodiments, methods of the invention comprise obtaining multiple milk samples from the subject at different time points, optionally wherein at least some of the multiple samples obtained at different time points are obtained from either or both breasts of the female subject.

In some embodiments, the method comprises measuring at least one physicochemical parameter of the milk sample obtained from the subject.

As a person of skill would understand, the method of the invention comprises obtaining a milk sample from the female subject at a time point and measuring at least one physicochemical parameter of the sample. The at least one physicochemical parameter may be measured by any means known in the art. In some embodiments, the at least one physicochemical parameter is measured using an electrochemical method or a spectroscopic method. As used herein, the method involves determining "an expression of the physicochemical parameter", namely the size (e.g., quantity, amount) of the physicochemical parameter. For example, where the parameter is at least one electrolyte, the expression of the parameter may involve the electrolyte presence and concentration. Where the parameter is conductance, the expression may be low or high conductance is measured.

In some embodiments, the at least one physicochemical parameter is one or more of (i) electrical resistivity, (ii) electrical conductivity, (iii) an amount of an electrolyte, (iv) an amount of a protein and (v) an amount of a sugar.

In some embodiments, the at least one physicochemical parameter is any such expression (presence/amount) relating to the electrolyte. Non-limiting examples of electrolytes that can be measured according to the invention include sodium, potassium, chloride, calcium, magnesium and phosphate ions.

In some embodiments, the electrolyte is sodium.

In some embodiments, the electrolyte is chloride.

In some embodiments, the at least one physicochemical parameter is the sample electrical resistivity or its inverse—electrical conductivity. Within the context of the invention, a low resistivity indicates a sample that is readily electrically conductive.

In some embodiments, the at least one physicochemical parameter is electrical conductivity.

The electrical conductivity and/or electrical resistivity may be measured by any method known in the art.

As measurements of experimental parameters may vary between one experimental setting to another, the measured parameters may be calibrated. Thus, in some embodiments, the method may further comprises obtaining the at least one physicochemical parameter and further calibrating the measured physicochemical parameter or normalizing the measured physicochemical parameter.

In some embodiments, normalization or calculating may comprise an operation according to Eq. (I) to obtain a computed value based on milk conductivity:

$$X' = \frac{x - x_{min}}{x_{max} - x_{min}} \quad \text{Eq. (I)}$$

wherein X' is an output computed value of at least one physicochemical parameter; X is the measured value or the calibrated measured value of the at least one physicochemical parameter at the first time point; $X_{min}$ is the minimal value of the same physicochemical parameter as in X and corresponds to the minimal value of this parameter as measured in the population of female subjects characterized by an adequate lactation or average value of the measured parameter minus 1.28SD at any time point after delivery, for example at any time point between 20 days to 40 days after delivery, in the population of female subjects characterized by an adequate lactation, optionally by exclusive lactation; $X_{max}$ is the maximum value of the same physicochemical parameter as in X and corresponds to the maximal value of this parameter as measured in the population of female subjects characterized by an adequate lactation or average value of the measured parameter plus 1.28SD at any time point after delivery, for example at any time point between 12 hours after delivery and 36 hours after delivery, in the population of female subjects characterized by an adequate lactation, optionally by exclusive lactation.

In some embodiments, normalization or calculating may comprise a function according to Eq. (II) to obtain maturation level based on milk conductivity:

$$X' = 1 - \frac{x - x_{min}}{x_{max} - x_{min}} \quad \text{Eq. (II)}$$

wherein X' is an output computed value of at least one physicochemical parameter; X is the measured value or the calibrated measured value of the at least one physicochemical parameter at a first time point; $X_{min}$ is the minimal value of the same physicochemical parameter as in X and corresponds to the minimal value of this parameter as measured in the population of female subjects characterized by an adequate lactation or average value of the measured parameter minus 1.28SD at any time point after delivery, for example at any time point between 20 days to 40 days after delivery, in the population of female subjects characterized by an adequate lactation, optionally by exclusive lactation; $X_{max}$ is the maximum value of the same physicochemical parameter as in X and corresponds to the maximal value of this parameter as measured in the population of female subjects characterized by an adequate lactation or average value of the measured parameter plus 1.28SD at any time point after delivery, for example at any time point between 12 hours after delivery and 36 hours after delivery, in the population of female subjects characterized by an adequate lactation, optionally by exclusive lactation.

It should be noted that any reference made herein to a value (measured value or a predetermined value) applies also for a calibrated and/or normalize or computed value.

As noted herein, methods of the invention comprise determining an expression of a physicochemical parameter of a breast milk sample obtained from the subject at a time point after delivery and determining an expression of the same physicochemical parameter of breast milk sample(s) obtained from adequately lactating subjects at the time point. Based on the two valuations, a determination is made as to whether the subject is adequately or inadequately lactating. The determination is thus based on data compiling physicochemical parameters collected from a population of adequately lactating female subjects (the control population). Adequate lactation in this population was determined based on objective and other measures in mothers of exclusively or predominantly breastfed or mother's milk fed infant, showing, for example, weight gain in the infant, number of stooling per day in the infant, number of urinating sessions per day in the infant, good physiological condition of the infant including good muscle tone, alertness and no signs of dehydration, as well as physiological or reported measures in the mother, such as volume of milk produced/transferred to baby, lack of nipple pain or breast infection, good breastfeeding evaluation, or lack of breastfeeding problems including low milk supply, tongue tie, or nipple/breast pain, as evaluated by a lactation consultant, and others. Some included measuring lactogenesis II at day 3-6 by an independent method. This population of female subjects includes more than 40 female subjects, more than 100 female subjects at times, or more than 300 female subjects.

The control population may be comprised of female subjects selected based on one or more population classifiers, including first delivery, multiparity, c-section, preterm birth, and others. Such sub-populations may be selectively used in providing determinations based on methods of the invention.

Based on the data collected from adequately lactating subjects, an expression of the physicochemical parameter may be predetermined for a specific time after infant delivery, such that any physicochemical parameter measure for a breast milk sample at a particular time point will have a corresponding expression in the dataset. This expression may be regarded as a predetermined expression of the parameter or a predicted parameter on the basis of which adequate or inadequate lactation may be determined.

In order to increase the accuracy and prediction capability, the predetermined value of the at least one physicochemical parameter is provided at the same time point as the time point of measurement, hence allowing an accurate comparison. The same time point as used herein encompasses essentially an identical time after delivery. Where the measurement is taken daily, 'same time point' refers to the hour of first measurement ±12 hours. Where the measurement is taken hourly, 'same time point' refers to the hour of the first measurement ±2 hours.

In some embodiments, the at least one physicochemical parameter is measured at a first time point between delivery and 14 days after delivery. Any further measurement may be conducted at any time thereafter essentially through the period of lactation. In some embodiments, the subsequent measurements may be carried out daily or hourly over the period of lactation.

In some embodiments, the at least one physicochemical parameter is measured at a first time point between delivery and 5 days after delivery. Any further measurement may be conducted at any time thereafter essentially through the period of lactation. In some embodiments, the subsequent measurements may be carried out daily or hourly over the period of lactation.

In some other embodiments, the at least one physicochemical parameter is measured at a first time point between infant delivery and 3 days after delivery. In some further embodiments, the at least one physicochemical parameter is measured at a first time point between infant delivery and 1 day after delivery.

In some embodiments, the at least one physicochemical parameter is measured at a first time point that is between 1 and 24 hours after delivery.

In some embodiments, the at least one physicochemical parameter is measured at a first time point between delivery and 72 hours after delivery.

In some further embodiments, the at least one physicochemical parameter is measured at a first time point between 48 hours after delivery and 72 hours after delivery.

In some embodiments, the at least one physicochemical parameter is measured at a first time point that is between 1 and 2 hours, or 3 hours, or 4 hours, or 6 hours, or 8 hours, or 10 hours, or 12 hours, or 15 hours, or 18 hours.

As known in the art, adequate lactation is a state of lactation characterized with an amount (volume) of milk secretion from the mammary glands that is essentially sufficient to meet the nutritional needs of an infant, while inadequate lactation is associated with an amount (volume) of milk secretion from the mammary glands that is insufficient to meet the nutritional needs of an infant. In accordance with the present invention, methods of the invention aim at predicting, determining, identifying or monitoring one or more expressions of "inadequate lactation", such as low milk supply, improper lactation initiation, delayed onset of lactogenesis II (DLII), inadequate lactogenesis III, a physiological complication in the mother and a physiological complication in an infant, or other related conditions such as breast inflammation and process of weaning from lactation.

In some cases, inadequate lactation is associated with or results in an inability to sustain exclusive breastfeeding.

Thus, in all methods, devices and systems of the invention inadequate lactation in a female subject comprises or is associated with at least one of reduced lactation efficiency, delayed lactogenesis II (DLII), inadequate lactogenesis III or reduced milk production.

While inadequate lactation may be determined using an expression of at least one physicochemical parameter measured at a first time point after delivery in a breast milk sample with respect to samples obtained from adequately lactating subjects, as discussed herein, in some embodiments, inadequate lactation may also be determined with respect to a second or sequential sample or samples obtained from the same subject at different time points (temporally-separated sample).

In some embodiments, the temporally-separated sample is a sample obtained prior to or after the first time point. Continuous monitoring of the same female subject allows constant monitoring of the lactation status, in a time scale of hours or days. This is beneficial for early detection of changes in the subject's health and lactation status. In accordance with some embodiments, the method comprises continuous monitoring of lactation of a female subject for early detection of inadequate lactation, see progress of lactation, and evaluate clinical or behavioral treatment effectiveness As described herein, a computational model may be used for methods of the invention. Such a model provides high temporal resolution information even within a few hours from delivery and can thus provide early diagnosis of various processes. An "early diagnosis" or "early detection" provides diagnosis prior to appearance of clinical symptoms, e.g., hours, days, weeks or even month before the appearance of such symptoms. As a person of skill would understand, methods and devices of the invention allow early determination of inadequate lactation, as defined, at a stage which precedes detection by other methods. Thus, early detection by employing methods of the invention can provide an indication of inadequate lactation before symptoms appear and may also exclude inadequate lactation where symptoms are observed and thus may be associated with a different cause.

Within the scope of the invention, early detection is not to be understood as a time point close to the day of delivery, but in fact may be regarded as any time point after delivery but prior to the appearance of symptoms. This time frame extending between delivery and point of early detection may be minutes, hours, days, weeks or months.

In some embodiments, methods for early detection are carried out when the female subject shows no appearance of symptoms.

In some embodiments, methods for early detection are carried out when symptoms such as pain, fever, swelling or other symptoms appear.

In some embodiments, the female subject is suffering from pain, swelling or fever, and methods of the invention are optionally adapted or used for determining whether the pain, swelling or fever are associated with inflammation/infection. Thus, any one method of the invention may be used for determining the likelihood of developing inadequate lactation in a female subject, the method comprising:

determining an expression of a physicochemical parameter of a breast milk sample obtained from the subject at a time point after delivery and after the development of pain, swelling or fever, and determining whether the subject is likely to develop inadequate lactation by comparing the expression of the physicochemical parameter of the breast milk sample with an expression of the physicochemical parameter of breast milk sample(s) obtained from adequately lactating subjects not suffering from pain, swelling or fever, at the same time point after delivery.

As fever, swelling and pain, each independently, may be indicative of or associated with a variety of medical conditions, e.g., infection or inflammation, methods of the invention may be used to determine whether such symptoms in the female subject are associated with inflammation or infection which, in some case, may result in inadequate lactation. Thus, to allow early treatment of inflammation or infection, methods of the invention may be used as a predictive or early diagnostic tool to determining whether the condition is likely to result in inflammation or an infection. For example, if a method of the invention provides an indication that an expression of a physicochemical parameter is different from that of the control population or changes over time with respect to an earlier sample, a determination may be made that the condition is likely to stem from an inflammation or an infection. Where such an indication is not observed, a determination may be made that the condition is likely not to stem from inflammation or infection.

In some embodiments, methods of the invention provide early detection of inadequate lactation, e.g. a low milk supply. In some embodiments, a low milk supply corresponds to a milk production in a volume lower than required by the baby for adequate growth (as clinically assessed by baby weight gain, growth rate, physiological condition, developmental assessment, milk transfer measured within a feed by direct or indirect methods).

In some embodiments, methods of the invention are adapted or are used for early diagnosis of inadequate lactation.

In another aspect of the invention, which may be implemented as certain embodiments of methods of the invention, provided is a method for early diagnosis of at least one of reduced lactation efficiency, delayed lactogenesis II (DLII), inadequate lactogenesis III or reduced milk production, the method comprising determining an expression of at least one of electrical resistivity or electrical conductivity of a breast milk sample obtained from the subject at a time point between delivery and 14 days after delivery, and determining whether the subject is suffering from at least one of reduced lactation efficiency, delayed lactogenesis II (DLII), inadequate lactogenesis III or reduced milk production, by comparing the expression of at least one of electrical resistivity or electrical conductivity of the breast milk sample with an expression of at least one of electrical resistivity or electrical conductivity of breast milk sample(s) obtained from adequately lactating subjects at the time point, wherein when the expression of least one of electrical resistivity or electrical conductivity measured for the breast milk sample and the expression of the of least one of electrical resistivity or electrical conductivity predetermined for the control population are not the same, the female subject is suffering from at least one of reduced lactation efficiency, delayed lactogenesis II (DLII), inadequate lactogenesis III or reduced milk production In another aspect of the invention, which may be implemented as certain embodiments of methods of the invention, provided is a method for early diagnosis of at least one of reduced lactation efficiency, delayed lactogenesis II (DLII), inadequate lactogenesis III or reduced milk production, the method comprising determining an expression of at least one of electrical resistivity or electrical conductivity of a breast milk sample obtained from the subject at a time point between delivery and 5 days after delivery, and determining whether the subject is suffering from at least one of reduced lactation efficiency, delayed lactogenesis II (DLII), inadequate lactogenesis III or reduced milk production, by comparing the expression of at least one of electrical resistivity or electrical conductivity of a breast milk sample with an expression of at least one of electrical resistivity or electrical conductivity of breast milk sample(s) obtained from adequately lactating subjects at the same time point, wherein when the expression of the at least one of electrical resistivity or electrical conductivity measured for the breast milk sample and the expression of the at least one of electrical resistivity or electrical conductivity predetermined for the control population are different, or the physicochemical parameter for the breast milk sample is outside a range defined by a standard deviation value of 1.285SD of the expression of the same physicochemical parameter predetermined for the control population, the female subject is suffering from at least one of reduced lactation efficiency, delayed lactogenesis II (DLII), inadequate lactogenesis III or reduced milk production.

In some embodiments, the method comprises an early diagnosis that the female subject is inadequately lactating based on the expression of electrical resistivity or an electrical conductivity of a breast milk sample obtained from the female at a time point between delivery and 14 days after delivery in comparison to an expression of an electrical resistivity or an electrical conductivity of breast milk sample(s) obtained from adequately lactating female subjects at the same time point between delivery and 14 days after delivery.

In some embodiments, methods of the invention aim at determining delayed lactogenesis II (DLII). Lactogenesis II is defined as the onset of copious milk production, which typically occurs between 48 and 72 h postpartum; onset after 72 h is considered delayed and is associated with unintended breastfeeding reduction and cessation.

Thus, delayed lactogenesis II is used to denote a longer than usual interval between the colostrum phase and copious milk production, but refers to situations that the mother has the ability to achieve full lactation. Failed lactogenesis II is a condition wherein the mother has failed to attain copious milk production (either due to intrinsic or extrinsic factors).

In some embodiments, delayed lactogenesis II corresponds to abnormal physicochemical parameter compare to expected at day 2-3 after birth.

Low milk supply or delayed lactogenesis may affect the infant health and may result in physiological complications. Therefore, it was suggested by the inventors that the method of the invention may be used to aid in diagnosing at least one physiological complication in an exclusively or predominantly breastfed infant. The physiological complication may be due to an inadequate milk intake due to inadequate lactation. In some embodiments, the physiological complication in the infant is at least one of inadequate or slow weight gain, weight loss, jaundice, feeding problems, failure to thrive, and dehydration.

Methods of the invention may also provide information on a physiological condition in the female subject, due to for example behavioral inadequacy or hormonal imbalance. This physiological complication may result in low milk production and/or delayed lactogenesis. In some embodiments, the method comprises early aid in the diagnosis of a physiological complication in the female subject. The physiological complication results with inadequate lactation.

In some embodiments, the physiological condition in the female subject is an hormonal imbalance, such as thyroid imbalance, prolactin imbalance and retained placenta, or inadequate breastfeeding behavior, reflected by improper breastfeeding frequency, improper breastfeeding session duration, and inefficient breastfeeding, such as improper latch, improper suckling by the baby on the breast or ineffective milk transfer In some further embodiments, physiological condition is a breast condition such as a breast engorgement, breast inflammation, breast infection and mastitis.

Methods for monitoring early diagnosis as detailed herein may be used for early diagnosis of any one of low milk production, delayed lactogenesis II, inadequate lactation, inability to sustain exclusive breastfeeding, physiological complications in the female mother or the infant by measuring at least one of electrical resistivity and/or electrical conductivity of a milk sample obtained from a lactating subject.

Methods of the invention are also suitable for following responsiveness of a female subject to a treatment at any time point after treatment commencement. Accordingly, the female may be evaluated at any time point after initiation of treatment in order to asses if the treatment protocol is efficient and appropriate. Determination can be carried out at an early stage such that a decision may be made regarding continuation of the treatment or alternatively readjusting the treatment protocol.

As stated herein, methods of the invention provide the ability to predict or determine the evolution of inadequate lactation at early stages. Methods of the invention further provide the ability to detect changes or determine profile of lactation over time in a female subject. Such diagnostic methods may be achievable by a device that measure the expression of a physicochemical parameters and further which determines whether the expression is indicative of adequate or inadequate lactation. The use of such devices may provide analysis within minutes from the time of sample collection and thus may permit facile and cost effective treatment at an early stage. Irrespective of the monitoring of inadequate lactation or a condition that is identified in the female subject, e.g., that is one or more of the following or that is associated with one or more of the following hormonal imbalance, such as thyroid imbalance, prolactin imbalance and retained placenta, a breast engorgement, breast inflammation, breast infection and mastitis, a device utilized in accordance with methods of the invention as well as methods which are carried out without using a device can provide dynamic information as to the development of the condition (improvement or worsening) over time.

In another aspect, there is provided a device for carrying out methods of the invention.

Devices of the invention enable safe and reliable measurement of at least one physicochemical parameter in a breast milk sample. The device may be a hand held device that allows breast milk collection and analysis and provides real time information relating to a variety of parameters, as detailed herein.

Also provided is a device for measuring at least one physicochemical parameter in a breast milk sample, the device comprising a chamber configured for holding a breast milk sample, a detector for determining an expression of at least one physicochemical parameter of the breast milk sample, a signal transmitting module and optionally a user interface.

In some embodiments, the device comprises a processor and a user interface.

In some embodiments, the device comprises a chamber configured for holding a breast milk sample, a detector for determining an expression of at least one physicochemical parameter of the breast milk sample (i.e., the expression being selected from the amount or size of said physicochemical parameter) and a signal transmitting module. The signal transmitting module is set for delivering the signal parameters to a processor (data processing unit) and a data user interface for delivering the results and insights. The processor and user interface are optionally part of the device.

In some embodiments, the at least one physicochemical parameter is at least one of (i) electrical resistivity, (ii) electrical conductivity, (iii) an amount of an electrolyte, (iv) an amount of a protein and (v) an amount of a sugar.

The invention further provides a system for determining inadequate lactation in a female subject, the system comprising a data processing unit for data communication with a physicochemical parameter sensor device according to the invention; a data user interface unit being in data communication with the data processing unit; wherein the data processing unit comprising data relating to at least one expression of a physicochemical parameter at various time points after infant birth and is adapted to receiving from the sensor device information relating to at least one expression of a measured physicochemical parameter of a breast milk sample obtained at a time point, and provide an indication of adequate or inadequate lactation.

In some embodiments, the device is a device according to FIG. 7.

As depicted in FIG. 7, a two-part device (100) is provided that comprises two detachable parts (measurement compartment 120 and sample chamber 130), when associated the parts form the full device. Each part of the device having a part of at least one electrode assembly, which parts (140 and 150) are connectable to form an electrode assembly which extends between the measurement compartment (120) and the sample chamber (130). The sample chamber (130) is configured to hold a sample of breast milk. Part (140) of the electrode assembly is positioned to permit contact with the sample in the sample chamber (130) and configured to form a direct contact with the part of the electrode assembly (150) positioned at the rim of the measurement compartment (120).

The device may further optionally comprise one or more securing mechanism (160), which may be in the form of a magnet and a corresponding magnetized surface (e.g., a metallized surface) or an adhesive surface, permitting reversible and secure association between the compartment (120) and chamber (130).

In some implementations of a device according to the invention, the device comprises an electrical sensor comprising at least one electrode assembly and a reader. In other implementations, the electrode assembly may be replaced with an antenna for measuring impedance.

In devices where the sensor is comprised of an electrode assembly and a reader, the electrode assembly may be constructed as explained with reference to the two-part device, wherein the reader, a power supply and other electronics as may be needed may be stored in the measurement compartment.

The electrode assembly is operably connected to the measurement compartment (120) or any component thereof in a manner that allows transmission of signals between the electrode assembly and the reader. For example, one or more electrodes can be used to determine an expression of a physicochemical parameter in a sample and convert that information into a signal.

The electrodes are configured to measure at least one physicochemical parameter in breast milk, being in accordance with some embodiments, electrical conductivity/resistivity.

Thus, the device described herein may be adapted or engineered for use in a method for determining inadequate lactation in a female subject, as disclosed herein. In some embodiments, the measurement compartment (120) further contains a signal transmitting module adapted for delivering signal parameters to a processor (data processing unit) and a user interface (such as a screen) for delivering the results and insights. The processor may be similarly part of the device and may be contained in the measurement compartment (120) or in an additional comportment (not shown). A user interface, e.g., screen or any other visualization means, may be provided on an external surface of either part of the device. In some embodiments, the device may be adapted for presenting the expression of the physicochemical parameter or an indication of adequate/inadequate lactation or any other message (numerical or alphabetic or by a color coding).

In other implementations of a device according to the invention, such as a device of FIG. 7, a data processing unit for data communication with the reader (in the measurement compartment 120) according to the invention and a data interface unit that is in data communication with the data processing unit are provided separately (externally). The processing unit may be at a remote location, e.g., a cloud, and comprising data relating to the at least one expression of a physicochemical parameter obtained from the control population, as disclosed herein, at various time points after infant birth and is adapted to receiving from the reader (via the signal transmitting module) information relating to the at least one expression of a measured physicochemical parameter of a breast milk sample obtained at a time point, and provide through the interface unit an indication of adequate or inadequate lactation, as disclosed.

In some embodiments, the indication of adequate or inadequate lactation, as defined, may be provided through an interface unit that is a remote device, e.g., an electronic device such as a cellphone, a computer or any portable device.

Sensing capabilities may be achieved by utilizing any sensor known in the art. The sensor may be an electrical sensor, an optical sensor or any other sensor. The sensors may be selected in accordance with the at least one physicochemical parameter to be measured and the sensitivity that is required for a particular physicochemical parameter. Where the device or part thereof is disposable, the sensor may be adapted for a single use. Where the device is intended for multiple uses, the sensor may be selected to undergo regeneration or rejuvenation between uses or to undergo calibration and re-calibration between sessions. Such regeneration/rejuvenation/calibration protocols are dependent on the sensor used and are known in the art. The term "sensor" refers, within the context of the present invention, to the components of a device configured to sense and transmit a data signal from the milk sample to the measurement units. As disclosed, the sensor may comprise at least one electrode assembly and at least one reader. In some embodiments, the sensor is adapted or selected as an analyte sensor, wherein that the data is obtained regarding the expression of the physicochemical parameter (namely the presence or concentration of an analyte) in a breast milk sample.

For the purpose if measuring current flow through the sample, a potentiostat may be used. The potentiostat may be any electrical element that applies a potential between a working and a reference electrode in an electrode assembly and measures the current flow through the working electrode.

Furthermore, to measure electrical resistance and electrical conductance suitable sensors that measure the resistance or conductance of the sample may be used.

The invention further provides methods of medical treatment or prophylaxis dependent on any one of the diagnostic methods disclosed herein. In general terms, the invention provides a method of treatment or management (including but not limited to further diagnostics, clinical assessment or follow-up) of a female subject diagnosed with inadequate lactation, the method comprising treating said subject with a therapeutic modality acceptable in the art.

In some embodiments, the method comprises identifying a female subject according to any method of the invention, as suffering from any one symptom or expression associated with inadequate lactation and treating said subject by means known in the art.

In some embodiments, the subject exhibits inflammation and is subsequently treated with anti-inflammatory medication.

The invention further provides a kit for carrying our methods of the invention, the kit comprising a chamber or a vile or container or a receptacle for holding a breast milk sample and a device for measuring at least one physicochemical parameters associated with the sample and instruction for use.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A shows the correlation between sodium in de-fatted breast milk (referred to as milk serum) and conductivity tested in whole milk by lab-grade conductivity meter, FIG. 1B shows the correlation between conductivity measured in low volume hand-held conductivity meter device according to the invention and conductivity measurements in a lab-grade conductivity meter for the same sample of breast milk. FIG. 1C shows the correlation between sodium in de-fatted breast milk (referred to as milk serum) and conductivity measured in low volume hand-held meter.

FIG. 5A are representative graphs from different mothers with 2 consecutive measurements with various time periods between the measurement, FIGS. 5B and 5C are examples of measurements of two individual mothers with repeated measurements along several weeks, each breast monitored separately, FIG. 5D shows a correlation in the same mother as shown in FIG. 5C, between pain intensity (upper panel) and the computed value (lower panel).

DETAILED DESCRIPTION OF EMBODIMENTS

Non-Limiting Examples

Example 1: Measurements of Conductivity and Sodium Concentration in Human Milk

Figure 1A:
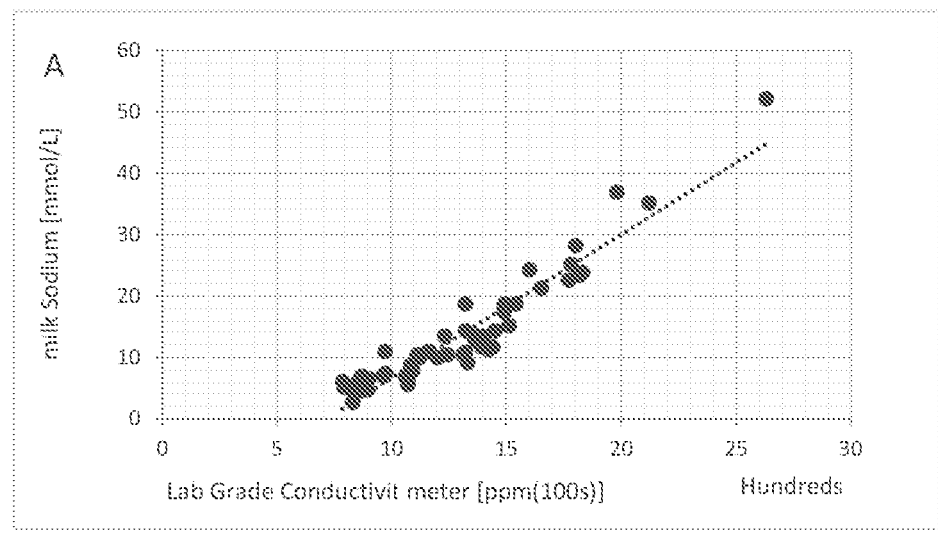
FIGS. 1A-1C are graphs showing the correlation between sodium concertation in breast milk samples and the conductivity measured in these samples.
Figure 1B:
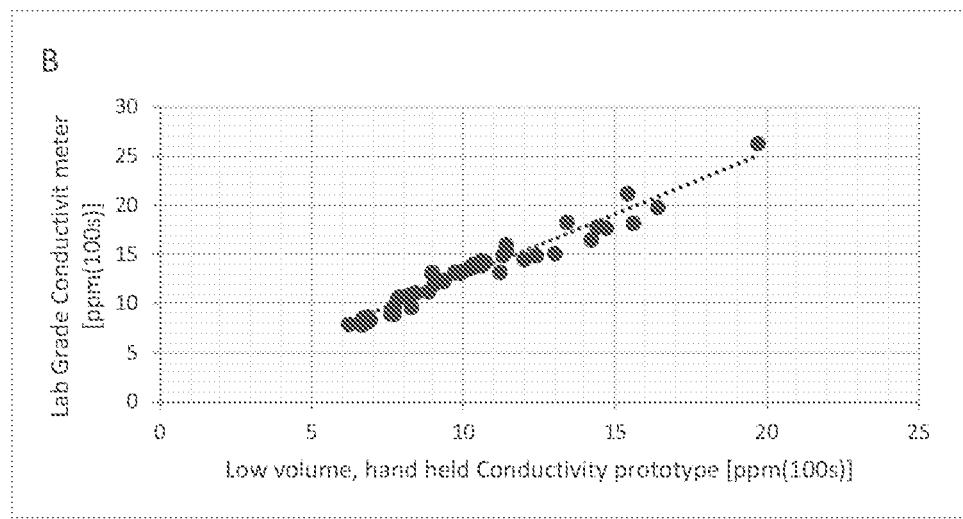
Figure 1C:
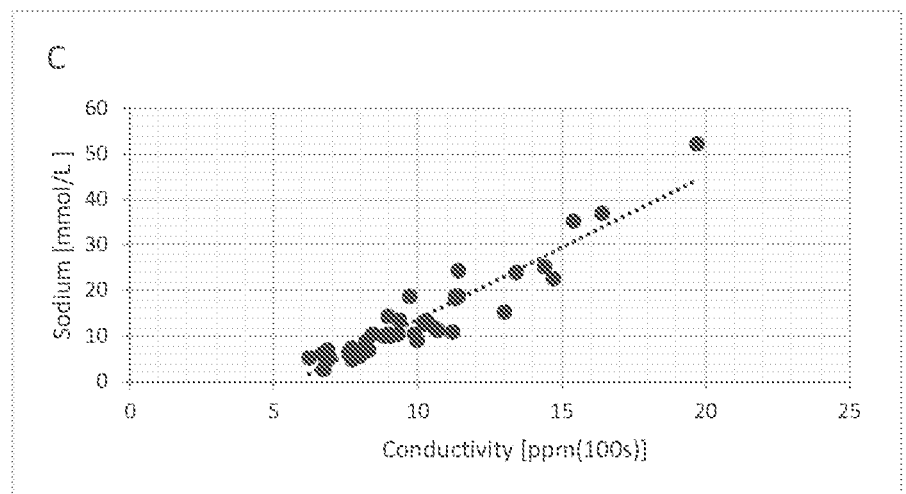

As shown in FIGS. 1A-1C, there is a linear correlation between the conductivity in human milk and the concentration of sodium of whole unprocessed milk samples. this correlation does not depend on the milk source (whole breast milk vs. de-fatted breast milk (centrifuge separated, referred to as "milk serum"), data not shown, and the type of the conductivity measurement.

Figure 2:
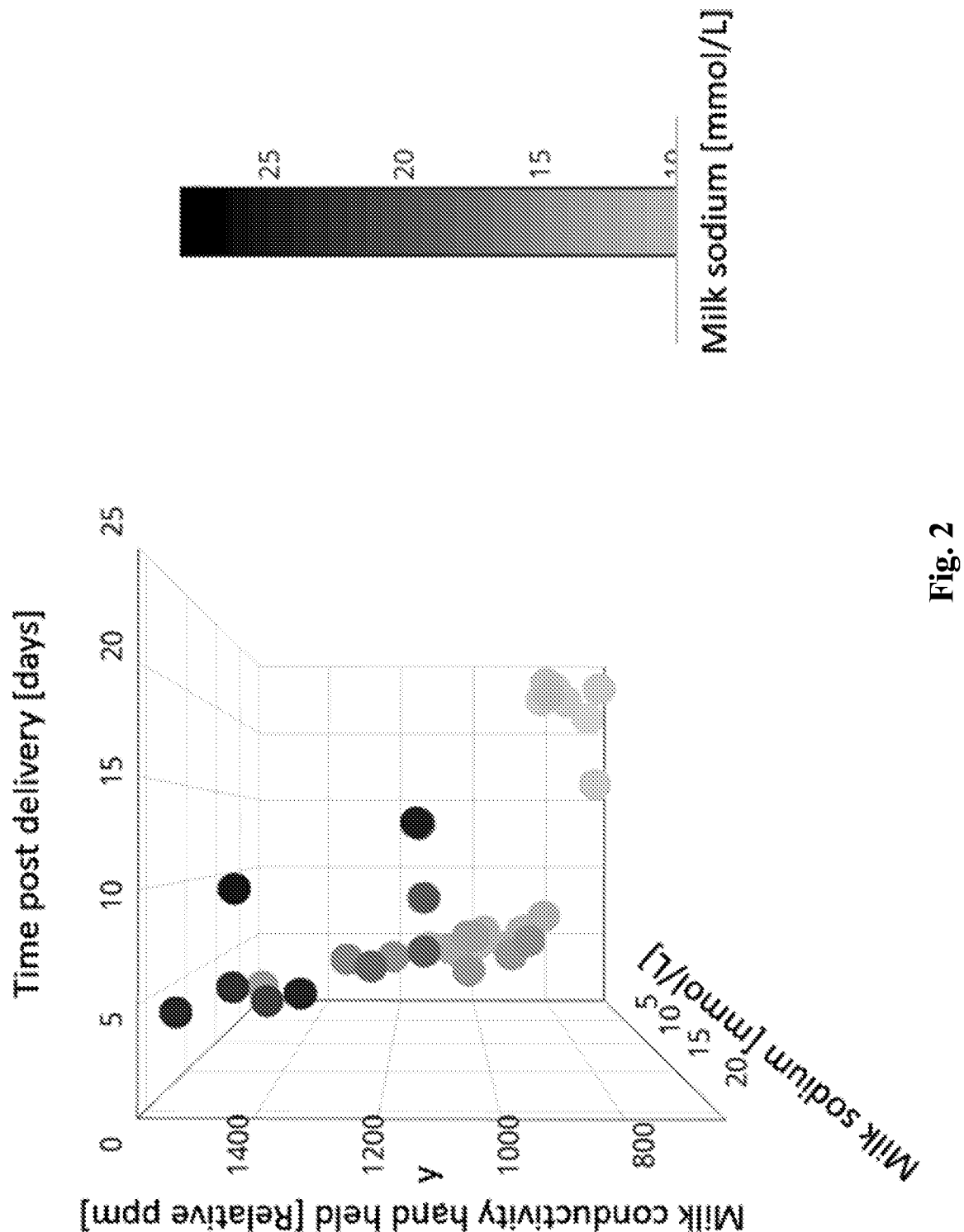
FIG. 2 is a graph showing the correlation between sodium concertation, conductivity and day post delivery. In the graph, the darker the dot is, the higher is the sodium concentration.

FIG. 2 shows a correlation between sodium concentration (Z axis, opacity), conductivity (Y axis) and day post delivery (X axis). As can be seen, there is a correlation between sodium levels, and milk conductivity and a dynamics across days postpartum.

Example 2: Determination of Lactation Status

Human breast milk samples at different days post-delivery were collected and tested in laboratory by hand held low volume milk sensing conductivity scanner and validated laboratory milk sodium human milk was also obtained.

The measured milk sodium levels were classified using a cutoff of 16 mmol/L, previously report to be a cutoff for assessing delayed lactogenesis on day 3 postpartum (Morton 1994), and breast pain symptom reported by maternal report.

Figure 3:
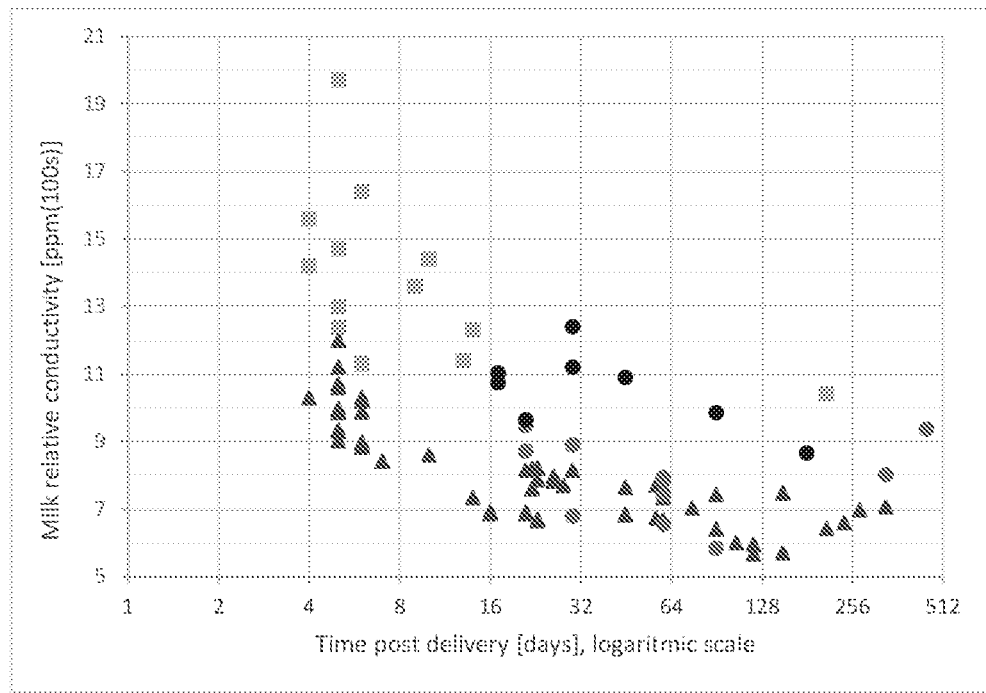
FIG. 3 shows classification of conductivity values vs. day from birth, based on measured milk sodium levels, in samples associated with breastfeeding pain (circle markers), and samples not associated with breastfeeding pain (square and triangle markers) using a cutoff value of 16 (a referenced indicator for delayed lactogenesis) such that square markers correspond to sodium concentration above 16, triangle markers correspond to sodium concentration below 16, and breast pain, black circles correspond to sodium concentration above 16 (and reported pain) and gray circles correspond to sodium concentration below 16 (and reported pain), data was obtained from 70 milk samples at different days post-delivery, samples were collected and tested in laboratories by conductivity scanner and validated laboratory test for milk sodium.

As can be seen in FIG. 3, conductivity of human milk is dynamically changing and can be determined based on exact day post delivery, and delayed lactogenesis can be identified based on conductivity. Pain is another condition that was shown here to be differentiated by conductivity of human milk in certain cases.

Based on the above, it can be suggested that breast milk conductivity as measured in a certain day after birth, can be used to determine breastfeeding and lactogenesis status, and pain can be further differentiated based on milk conductivity Example 3: Prediction of Lactation Status Based on the conductivity data and time elapsed from an event (set as delivery time in this example), an algorithm based on milk index table was developed and was clinically assessed to predict breastfeeding success and milk supply based on mother own milk sample. Relative normalized conductivity was measured by lactation consultants at the point of care or mothers' home, the system computed breastfeeding adequacy (% maturation, predicted age of milk, color).

System sensitivity, efficiency and accuracy relative to the clinical evaluation by face-to-face meeting with lactation consultant was assessed retrospectively on the dataset in 124 women post delivery. The women were assed at 4 days to 3 month with 88% of the women assed within first month up to a total of one year.

The computed milk maturation index alerts (output of the developed algorithm,) was compared to score of a lactation consultant after face-to-face evaluation of suspected low milk supply, and/or pain beyond 5 days postpartum, and/or reported non-exclusively breastfeeding.

The computed milk maturation alerts preliminary analysis revealed sensitivity of 73% (true positive identification) and specificity of 80% (true negative), with a positive predictive value (PPV) of 92%.

Positive is identification of at least one of low milk supply, and/or pain beyond 5 days postpartum, and/or reported non-exclusively breastfeeding, PPV is a statistic measure in clinical diagnostics—how many of the positively identified by the system are true positives.

All in all, The system was tested about 500 women after birth. Conductivity measurements were obtained from the women at different days post delivery, ranging from 1 day after birth to 350 days after birth using the device described herein. For each milk sample, a milk maturation % was calculated using the developed algorithm.

Figure 4:
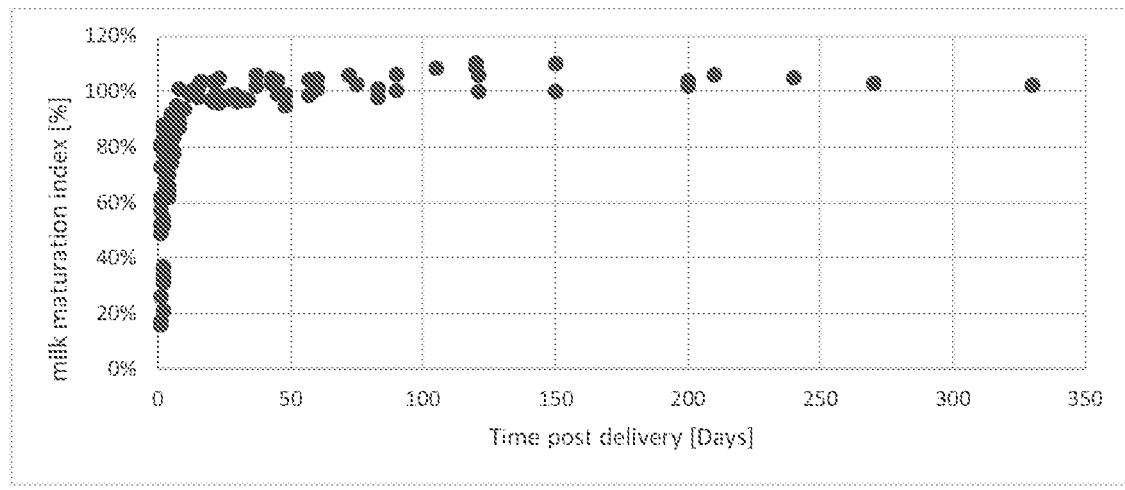
FIG. 4 is a graph showing breast milk maturation index as a function of time after delivery.

FIG. 4 shows the algorithm behavior in breast milk samples that were collected from exclusive breastfed women, with no breastfeeding problems, at various stages after delivery. The Y axis corresponds to computed milk maturation index that was calculated based on milk raw data by conductivity sensor and presented as percentages on the full range from early colostrum (0%) to mature milk (100%) conductivity.

Figure 5A:
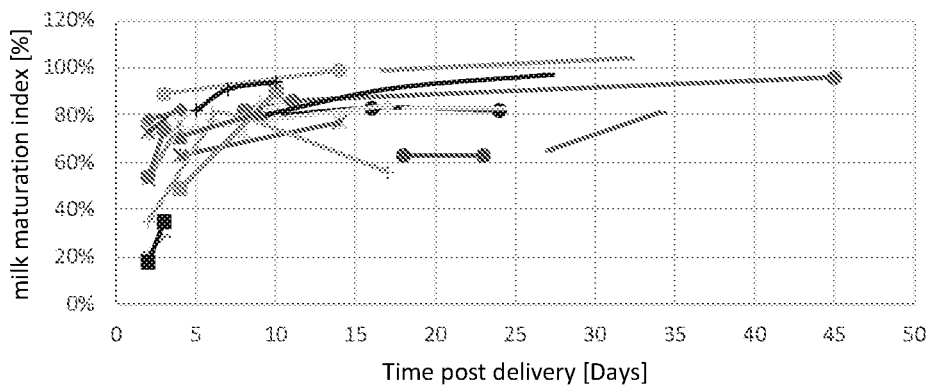
FIGS. 5A-5D show individual mother's milk dynamic analysis.
Figure 5B:
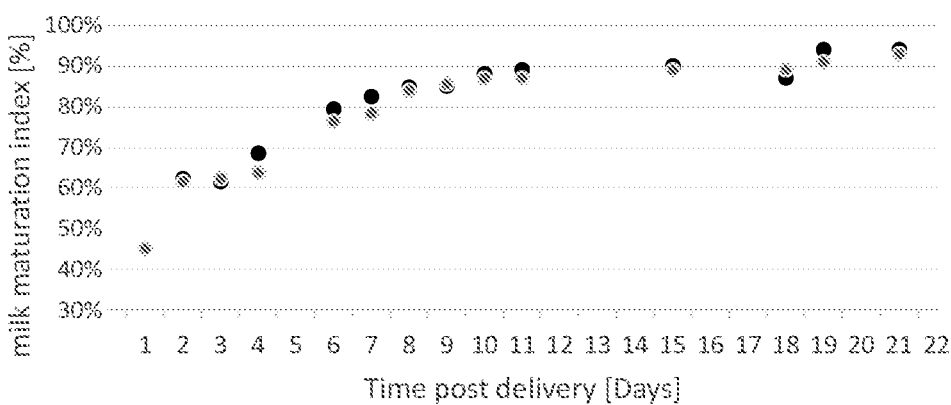

For some of the tested women, more than a single sample was obtained and hence intra-subject information can be obtained between different time point (e.g. slope between points). As shown in FIG. 5A. It was suggested that a model integrating such inter-subject data can be used for increasing sensitivity and specificity for prediction power. The data from the two breast is shown for two different women in FIGS. 5B and 5C.

Figure 5C:
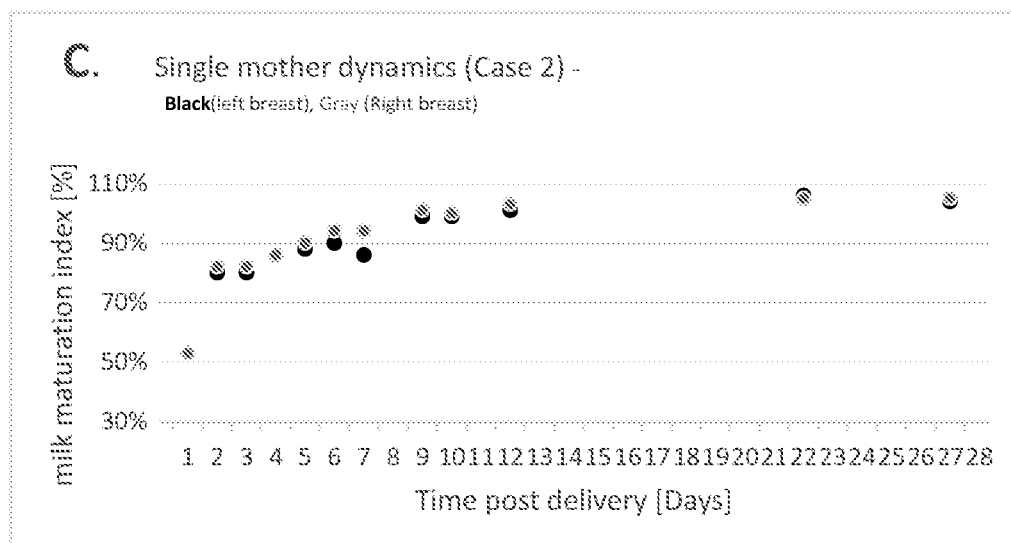
Figure 5D:
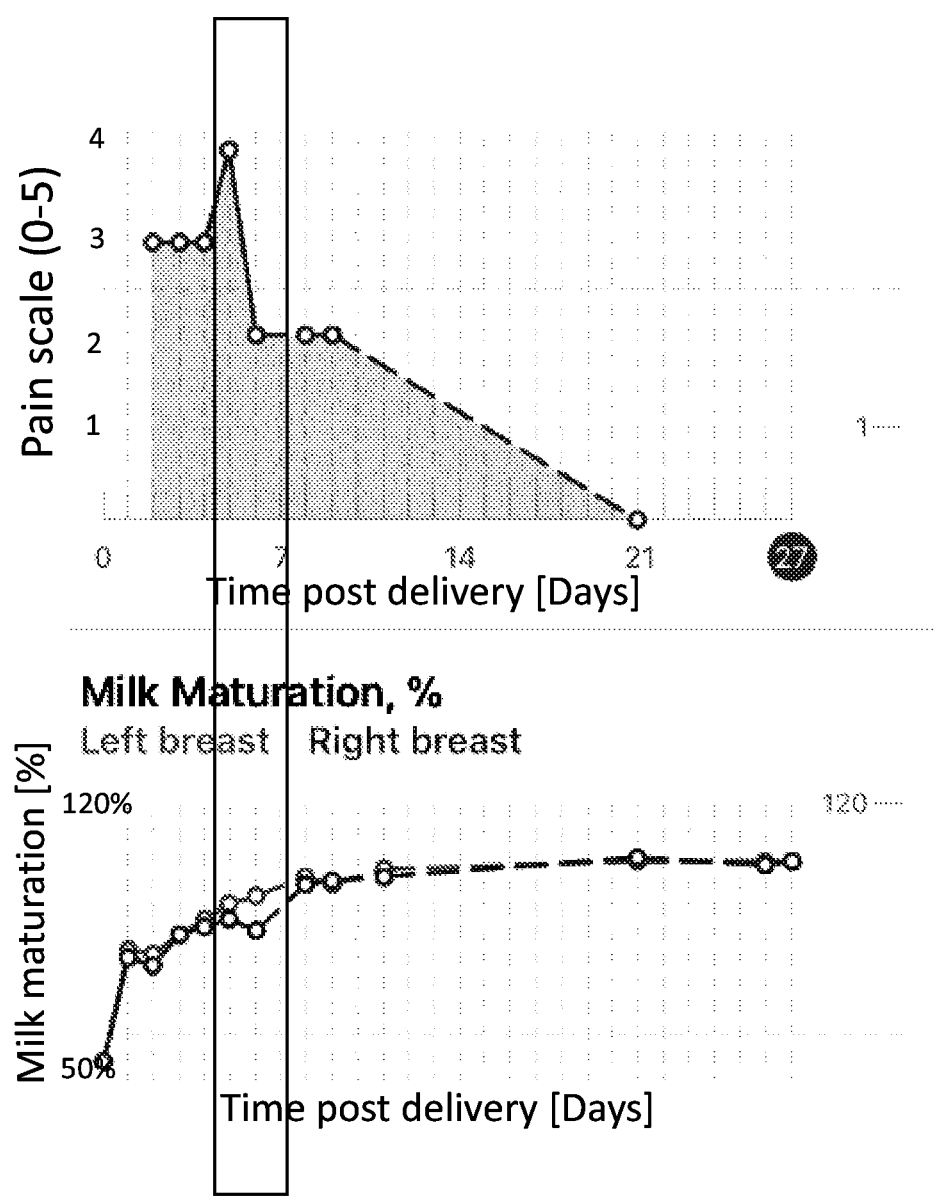

FIG. 5C shows that at day 7 after delivery only in one of the breasts there is a slight decrease in the model output and this was correlated to the mother condition, i.e. pain. As can be seen in FIG. 5D, an increase in pain was observed at the same time point as the decrease observed in FIG. 5C. these data indicate the ability to identify pain that was attributed by a lactation specialist to a transient inflammatory process, identified by the minor differentiation between-breast of dynamics of the maturation index calculated based on milk conductivity measured and computed by the system on days 6-8 postpartum, that was resolved by day 8-9 postpartum.

FIGS. 6A-6D depict maturation % and classification made by in accordance to feeding type and complications report by lactation consultants, using the following four criteria:
  (i) Exclusive OK—Exclusive breastfeeding correspond to breastmilk samples obtained from mothers with no particular breastfeeding concerns (dark circle, grey),
  (ii) Formula—significant formula feeds introduced (x, light grey), at least 30% Intermediate conditions:
  (iii) predominant but problems—predominant breastfeeding with reported breastfeeding problems
  (iv) Exclusive but problems—Exclusive breastfeeding with reported breastfeeding problems
  (v) predominant OK—predominantly about 80% breastfeeding with some formula introduced without reported breastfeeding problems.

Figure 6A:
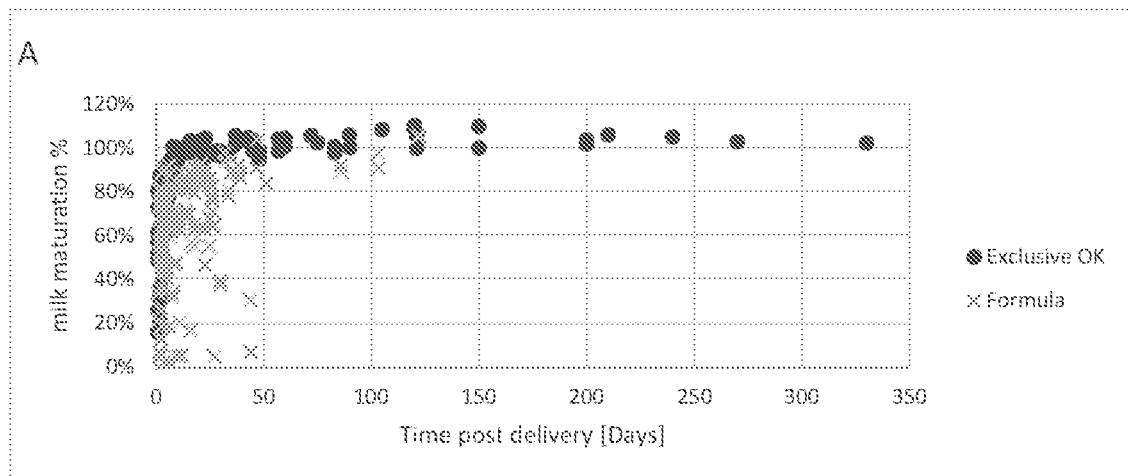
FIGS. 6A-6D are graphs showing the accuracy of prediction of lactation status using the developed algorithm, breast milk samples from over 400 mothers were collected at various day post delivery processes and analyzed to obtain milk maturation %, samples are classified into four groups based on lactation consultant and mothers' report: (i) exclusive breastfeeding, (ii) non-exclusive breastfeeding, (iii) predominant mothers milk but lactation problem and (iv) predominant mothers milk, no reported problems (OK), FIG. 6A. shows milk maturation % classified into two group in breast milk samples collected up to 1 year post delivery, FIG. 6B. same classification as in FIG. 6A limited to samples up to 50 days post delivery, FIG. 6C. shows milk maturation % classified into four group in breast milk samples collected up to 1 year post delivery, FIG. 6D. same classification as in FIG. 6C limited to samples up to 25 days post delivery.
Figure 6B:
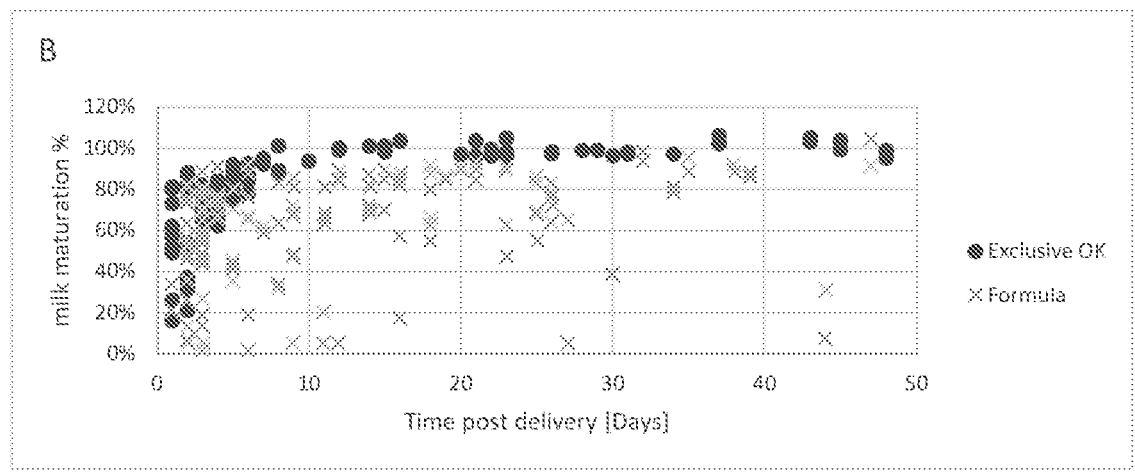

FIG. 6A shows calculated milk maturation % for two groups (i) exclusive breastfeeding and (ii) significant formula feeding in breast milk samples collected up to 1 year post delivery, FIG. 6B is the same figure as in FIG. 6A limited to 50 days post delivery.

Figure 6C:
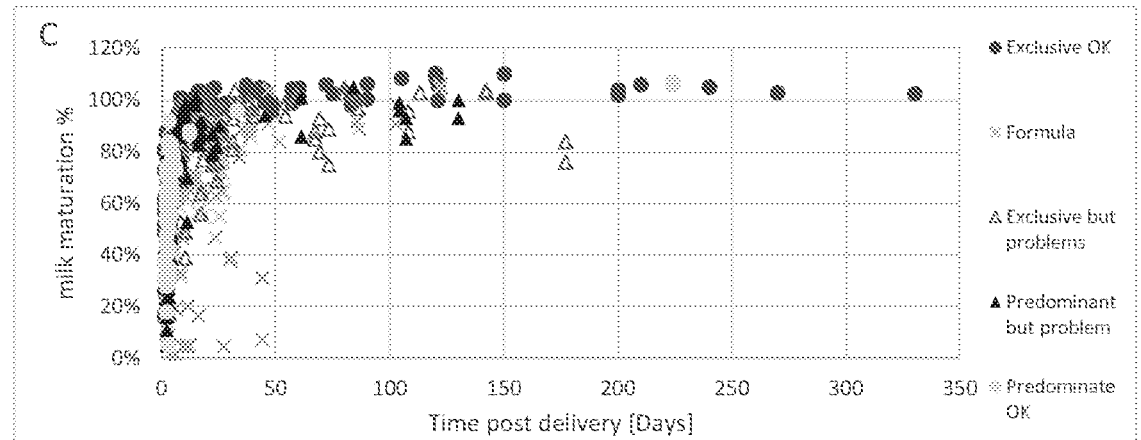
Figure 6D:
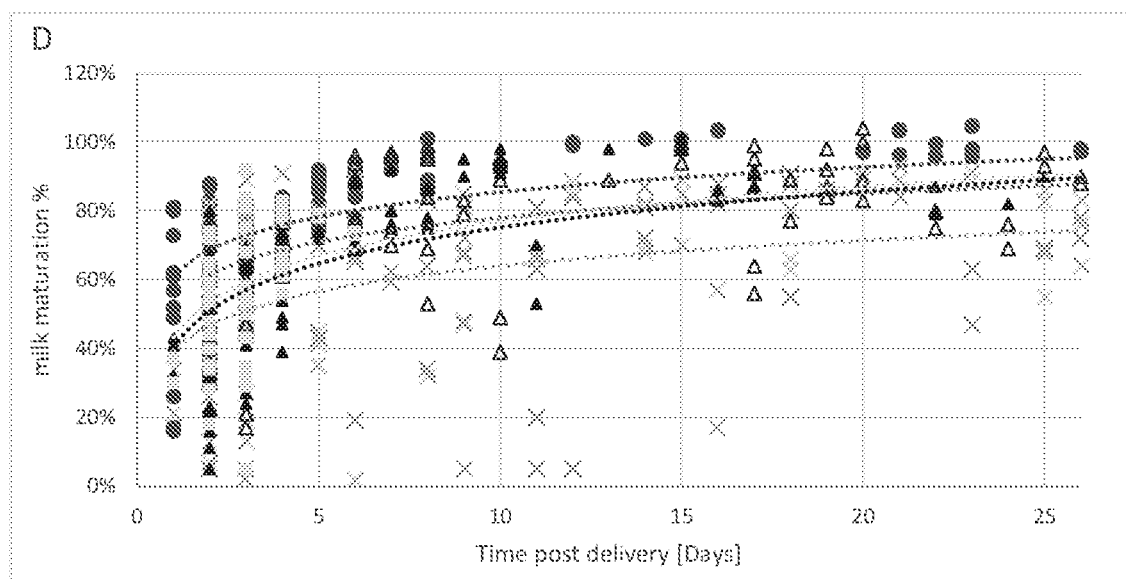
Figure 7:
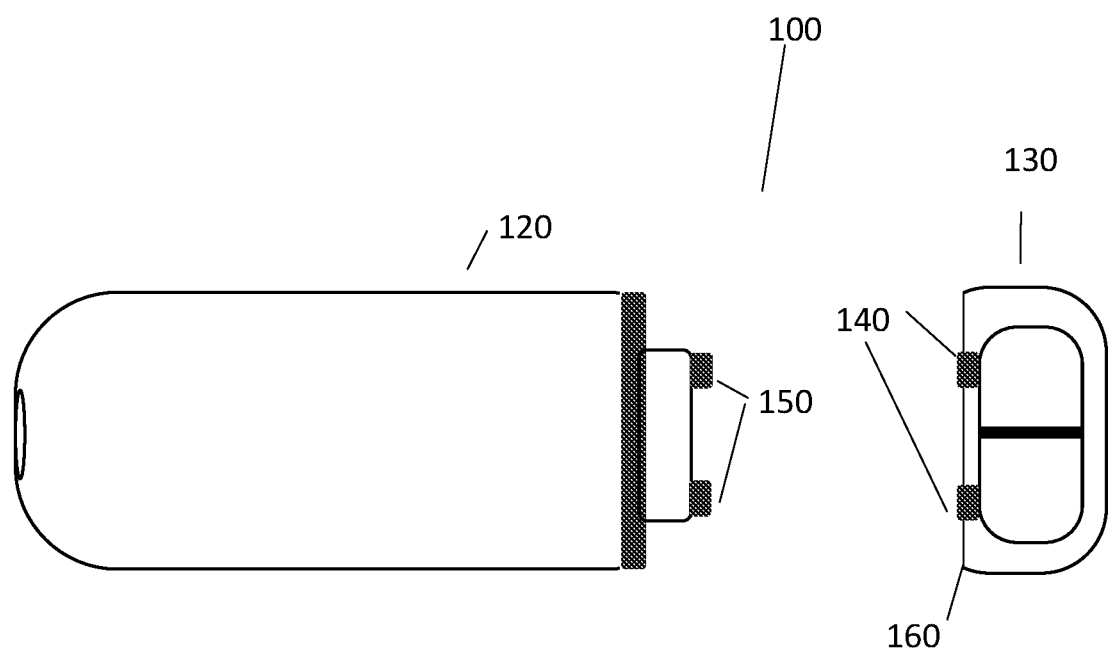
FIG. 7 shows a schematic representation of a device in accordance with some embodiments.

FIG. 6C shows calculated milk maturation % for four groups detailed above in breast milk samples collected up to 1 year post delivery, FIG. 6D is the same figure as in FIG. 6C limited to 25 days post delivery.

As can be seen, milk maturation as calculated can differentiate between significant formula of over 30% of feeds in breastfeeding mothers, such mothers with reported breastfeeding problems and exclusive breastfeeding without reported problems. The intermediate cases can be further classified based on maturation calculated, to resemble any of the aforementioned groups.

The invention claimed is:

1. A method for determining inadequate lactation in a female subject, the method comprising:
  determining an expression of a physicochemical parameter of one or more breast milk sample(s) obtained from the female subject at one or more time point(s) after delivery,
  determining a milk maturation percent calculated on the physicochemical parameter of the one or more breast milk sample(s), said milk maturation percent reflects the level of milk maturation of the breast milk sample (s) on a scale ranging between early colostrum (0%) and mature milk (100%) of said physicochemical parameter;
  determining whether the female subject is inadequately lactating by comparing the expression of the physicochemical parameter and/or the milk maturation percent of the one or more breast milk sample(s) of said female subject with an expression of the physicochemical parameter and/or the milk maturation percent of one or more breast milk sample(s) obtained from a control population of adequately lactating subjects at the same one or more time point(s) after delivery;
  wherein when the expression of the physicochemical parameter and/or the milk maturation percent measured for the one or more breast milk sample(s) of said female subject and the expression of the physicochemical parameter and/or the milk maturation percent predetermined for the one or more breast milk sample(s) of the control population at the same time point(s) after delivery are not the same, the female subject has inadequate lactation or is likely to develop inadequate lactation; and
  wherein inadequate lactation comprises reduced lactation efficiency, delayed lactogenesis II (DLII), inadequate lactogenesis III, reduced milk production, and/or breast inflammation.

2. The method of claim 1, wherein when the expression of the physicochemical parameter of the one or more breast milk sample(s) of the female subject and the expression of the physicochemical parameter of the one or more breast milk sample(s) of the control population are the same, or the expression of the physicochemical parameter of the one or more breast milk sample(s) of the female subject is within 1.285 standard deviation (SD) of the expression of the same physicochemical parameter of the one or more breast milk sample(s) of the control population for the same time point(s) after delivery, the female subject has adequate lactation.

3. The method according to claim 1, for determining inadequate lactation in one or in both breasts of the female subject.

4. The method according to claim 1, wherein the one or more breast milk samples obtained from the female subject at the one or more time points after delivery comprises multiple breast milk samples from the female subject obtained at different time points after delivery, and wherein at least some of the multiple breast milk samples obtained at different time points after delivery are obtained from either or both breasts of the female subject, and calculating the change or difference between any two of the multiple breast milk samples.

5. The method according to claim 1, comprising measuring the physicochemical parameter of at least one of the one or more breast milk sample(s) obtained from the female subject at a time point of the one or more time points between delivery and 14 days after delivery.

6. The method according to claim 1, wherein the physicochemical parameter is at least one of (i) electrical resistivity, (ii) electrical conductivity, (iii) an amount of an electrolyte, (iv) an amount of a protein and (v) an amount of a sugar.

7. The method according to claim 6, wherein the at least one physicochemical parameter is electrical resistivity or electrical conductivity.

8. The method according to claim 1, for early diagnosis of at least one of inadequate lactation, reduced lactation efficiency, delayed lactogenesis II (DLII), inadequate lactogenesis Ill or reduced milk production, the method comprising:
determining an expression of at least one of electrical resistivity or electrical conductivity of the one or more breast milk sample(s) obtained from the female subject at a time point of the one or more time points between delivery and 14 days after delivery, and
determining whether the female subject is suffering or having likelihood of developing at least one of reduced lactation efficiency, delayed lactogenesis II (DLII), inadequate lactogenesis III, and/or reduced milk production, by comparing the expression of the at least one of electrical resistivity or electrical conductivity of the one or more breast milk sample(s) with an expression of at least one of electrical resistivity or electrical conductivity of the one or more breast milk sample(s) obtained from the control population of adequately lactating female subjects at the time point, wherein when the expression of the at least one of the electrical resistivity or electrical conductivity measured for the one or more breast milk sample(s) and the expression of the at least one of the electrical resistivity or electrical conductivity predetermined for the one or more breast milk sample(s) of the control population are not the same, the female subject is suffering from or having likelihood of developing at least one of reduced lactation efficiency, delayed lactogenesis II (DLII), inadequate lactogenesis III, and/or reduced milk production.

9. The method according to claim 8, wherein the time point is at a time point between delivery and 5 days after delivery.

10. The method according to claim 1, wherein the female subject is suffering from breast pain, swelling and/or fever, and wherein the method-further comprises determining that said female subject has or is likely to develop breast inflammation when said female subject has inadequate lactation and suffers from breast pain, swelling and/or fever; or wherein the method further comprises determining that said female subject has or is likely to develop breast inflammation when said female subject suffers from breast pain, swelling and/or fever and there is a decrease in the milk maturation percent over time between earlier and later samples of the same breast of said female subject and/or there is a difference between samples from both breasts taken at the same time point after delivery.

11. A device for carrying out a method according to claim 1, by measuring the expression of at least one physicochemical parameter selected from a group consisting of conductivity, resistivity, and/or an amount of an electrolyte in the breast milk sample of the female subject, the device comprising
a milk sample chamber configured for holding the breast milk sample; and
a measurement compartment comprising at least one electrode assembly configured to measure said expression of said at least one physicochemical parameter of said breast milk sample, a signal transmitting module, a data processing unit for carrying the comparison to said control population, and a user interface unit for delivering the results, the milk maturation percent, progress of lactation, an indication of adequate/inadequate lactation, and insights,
wherein the data processing unit is configured for data communication with the at least one electrode assembly and the user interface, wherein the data processing unit comprising stored data relating to the conductivity and/or resistivity and/or the amount of electrolyte measurements of the breast milk sample(s) of the control population at the one or more time point(s) after delivery and is adapted to receiving via the signal transmitting module information relating to the conductivity and/or resistivity and/or amount of electrolyte measurement(s) of the breast milk sample, and provide through the user interface unit the indication of adequate or inadequate lactation;
wherein the measurement compartment and the milk sample chamber are connectable, wherein the at least one electrode assembly extends between the measurement compartment and the milk sample chamber such that it is configured to form a direct contact with the breast milk sample in the milk sample chamber when the milk sample chamber and the measurement compartment are connected;
wherein the device is a handheld device and configured for repeated breast milk sample sampling and monitoring of lactation of a female subject within minutes.

12. The device according to claim 11, wherein the data processing unit is configured for calculating the milk maturation percent and presenting said milk maturation percent on the user interference.

13. The device according to claim 11, wherein the user interface unit is configured for presenting that the female subject has or is likely to develop breast inflammation when said female subject is determined by the device to have inadequate lactation and is further suffering from breast pain, swelling and/or fever, or when said female subject suffers from breast pain, swelling and/or fever and there is a decrease in the milk maturation percent over time between earlier and later samples of the same breast of said female subject and/or there is a difference between samples from both breasts taken at the same time point after delivery.

14. The device according to claim 13, wherein the data processing unit is a remote data processing unit selected from a cellphone, a computer or a portable device, and wherein the device further comprises a data processing unit within the device.

15. The method according to claim 1, for daily measuring the expression of the physicochemical parameter of the breast milk samples obtained from the female subject and comparing the same to the expression of the physicochemical parameter of the breast milk samples obtained from the control population at the same day after delivery.

16. The method of claim 1, further comprising comparing the time point after delivery at which the expression of the physicochemical parameter is measured to a time point after delivery of a breast milk sample of the control population having a similar value of expression of the physicochemical parameter, wherein when the time point after delivery of the breast milk sample of the female subject and the time point after delivery of the breast milk sample of the control population having a similar value of expression of the physicochemical parameter are substantially identical, the female subject has adequate lactation.

17. The method according to claim 1, for determining the likelihood of developing inadequate lactation in the female subject, wherein the one or more breast milk sample(s) are multiple breast milk samples obtained from the female subject at multiple time points after delivery from the same or from different breasts, and determining whether the female subject is likely to develop inadequate lactation by comparing the expression of the physicochemical parameter of the breast milk samples at the multiple time points after delivery or by comparing the expression of the physicochemical parameter of the breast milk samples from the different breasts.

18. A method for determining inadequate lactation in a female subject, the method comprising:

determining an expression of a physicochemical parameter of multiple breast milk samples obtained from the female subject at multiple time points after delivery, determining a milk maturation percent calculated on the physicochemical parameter of the multiple breast milk samples, said milk maturation percent reflects the level of milk maturation of the breast milk samples on a scale ranging between early colostrum (0%) and mature milk (100%); and determining whether the female subject is inadequately lactating by comparing a change in the expression of the physicochemical parameter and/or a change in the milk maturation percent of the breast milk samples of the female subject with a change in an expression of the physicochemical parameter and/or a change of a milk maturation percent of breast milk samples obtained from a control population of adequately lactating female subjects at the same time points after delivery;

wherein when the change in the expression of the physicochemical parameter and/or the milk maturation percent measured for the breast milk samples of said female subject and the change in the expression of the physicochemical parameter and/or the milk maturation percent predetermined for the breast milk samples of the control population at the same time points after delivery are not the same, the female subject has inadequate lactation or is likely to develop inadequate lactation; and wherein inadequate lactation comprises reduced lactation efficiency, delayed lactogenesis II (DLII), inadequate lactogenesis III, reduced milk production, and/or breast inflammation.

19. A device for carrying out a method according to claim 18, by measuring the change in the expression of at least one physicochemical parameter selected from the group consisting of conductivity, resistivity, and/or an amount of an electrolyte in the breast milk samples of the female subject, the device comprising a milk sample chamber configured for holding the breast milk sample; and a measurement compartment comprising at least one electrode assembly configured to measure said change in the expression of said at least one physicochemical parameter of said breast milk sample, a signal transmitting module, a data processing unit for carrying the comparison to said control population, and a user interface unit for delivering the results, the milk maturation percent, the progress of lactation, an indication of adequate/inadequate lactation, and insights, wherein the data processing unit is configured for data communication with the at least one electrode assembly and the user interface, wherein the data processing unit comprising stored data relating to the change in conductivity and/or resistivity and/or the amount of electrolyte measurements of the breast milk sample(s) of the control population at the one or more time point(s) after delivery and is adapted to receiving via the signal transmitting module information relating to the conductivity and/or resistivity and/or amount of electrolyte measurement(s) of the breast milk sample(s), calculate the change from a previous sample and provide through the user interface unit the indication of adequate or inadequate lactation;

wherein the measurement compartment and the milk sample chamber are connectable, wherein the at least one electrode assembly extends between the measurement compartment and the milk sample chamber such that it is configured to form a direct contact with the breast milk sample in the milk sample chamber when the milk sample chamber and the measurement compartment are connected;

wherein the device is a handheld device and configured for repeated breast milk sample sampling and monitoring of lactation of a female subject within minutes.

* * * * *